United States Patent
Rothbarth et al.

[11] Patent Number: 6,117,125
[45] Date of Patent: Sep. 12, 2000

[54] METHOD FOR PREDETERMINING UNIFORM FLOW RATE OF A FLUID FROM A TUBULAR BODY AND DEVICE THEREFROM

[75] Inventors: Leo Rothbarth, Englewood, Colo.; Frank J. Miller, Salt Lake City, Utah; Joseph F. Ely, West Lafayette; David St. John, Bloomington, both of Ind.

[73] Assignee: Cook Incorporated, Bloomington, Ind.

[21] Appl. No.: 08/640,543

[22] Filed: May 2, 1996

[51] Int. Cl.$^7$ .................................................. A61M 25/00
[52] U.S. Cl. ............................................ 604/523; 604/264
[58] Field of Search .................................... 604/264, 280

[56] References Cited

U.S. PATENT DOCUMENTS

| | | |
|---|---|---|
| 3,658,053 | 4/1972 | Fergusson et al. . |
| 3,888,249 | 6/1975 | Spencer . |
| 4,173,981 | 11/1979 | Mortensen . |
| 4,186,745 | 2/1980 | Lewis et al. . |
| 4,299,226 | 11/1981 | Banks . |
| 4,364,394 | 12/1982 | Wilkinson . |
| 4,406,656 | 9/1983 | Hattler et al. . |
| 4,538,621 | 9/1985 | Jarczyn . |
| 4,543,087 | 9/1985 | Sommercorn et al. ............. 604/264 |
| 4,717,379 | 1/1988 | Ekholmer . |
| 4,748,984 | 6/1988 | Patel . |
| 4,782,834 | 11/1988 | Maguire et al. . |
| 4,795,439 | 1/1989 | Guest . |
| 4,801,297 | 1/1989 | Mueller . |
| 4,995,865 | 2/1991 | Gahara et al. . |
| 5,021,044 | 6/1991 | Sharkawy . |
| 5,069,673 | 12/1991 | Shwab .................................. 604/280 |
| 5,149,327 | 9/1992 | Oshiyama . |
| 5,304,155 | 4/1994 | Lui . |
| 5,425,723 | 6/1995 | Wang . |

FOREIGN PATENT DOCUMENTS

| | | |
|---|---|---|
| 9407549 | 4/1994 | WIPO . |

OTHER PUBLICATIONS

Hannum, B., Pearson, Prof. J.T., "Calculation of Hole Sizes for Equal Flow," Purdue University Technical Assistance Program, Aug. 1, 1994, pp. 1–9.

*Primary Examiner*—Michael Buiz
*Assistant Examiner*—Daphna Shai
*Attorney, Agent, or Firm*—Richard J. Godlewski

[57] ABSTRACT

A method for predetermining the controlled and uniform discharge rate of a fluid from a single lumen tubular body having passageways radially extending through the wall of the tubular body has been developed and is described. The method involves predetermining such parameters as the transverse cross-sectional areas of the passageways extending through the wall of the tubular body, the spacing of the passageways, the pressure at each of the passageways, and the rate of flow at each of the passageways. One specific preferred application of such a tubular body is an infusion catheter for delivering various fluids to designated areas of the body for either a therapeutic treatment and/or diagnostic purposes. For example, such a catheter may be adapted to deliver controlled and uniform quantities of thrombolytic agents, chemotherapeutic agents as well as such diagnostic agents as fluorescent dyes and radioactive agents.

30 Claims, 1 Drawing Sheet

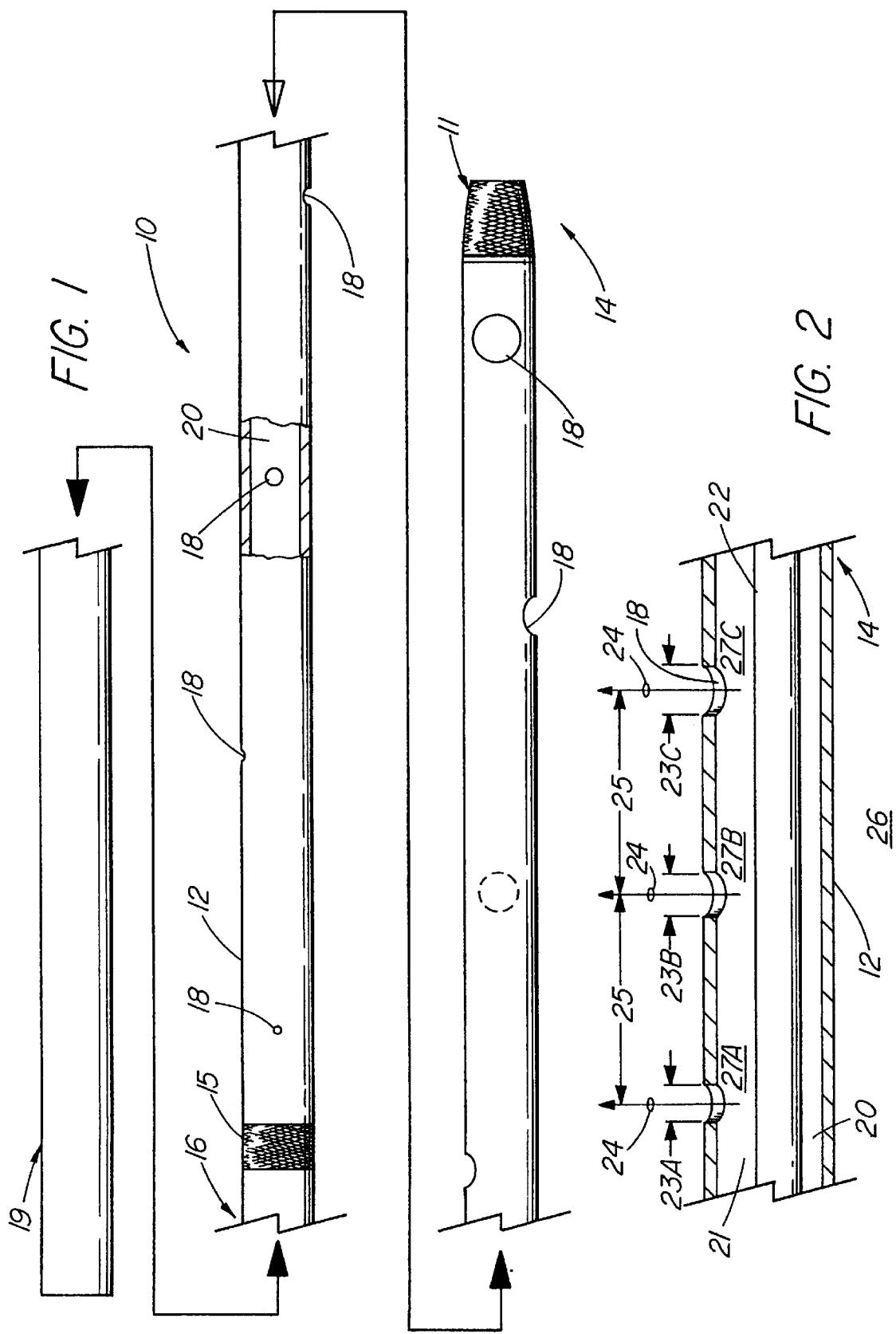

METHOD FOR PREDETERMINING UNIFORM FLOW RATE OF A FLUID FROM A TUBULAR BODY AND DEVICE THEREFROM

TECHNICAL FIELD

The present invention relates generally to a method for predetermining a uniform flow rate of a fluid from a tubular body and medical devices derived from such a method. More specifically, the invention relates in one embodiment to an infusion catheter useful in the delivery of various fluids into the human body at a uniform discharge rate.

BACKGROUND OF THE INVENTION

In certain medical conditions, it is advantageous to deliver a therapeutic agent directly to a target region to avoid medicating the entire body and to limit the amount of therapeutic agent required for effective treatment. Alternatively the same objective may be desirable for a diagnostic agent. One example of such a medical condition is an arterial thrombus, or clot, which can be treated effectively by localized application of such therapeutic fluids as those containing tissue plasminogen activator, urokinase, or streptokinase.

Infusion catheters have been developed which can deliver therapeutic fluids directly to affected bodily passages, for example a thrombotic region of an artery. One type of infusion catheter is a hollow tube, the distal end of which has been pierced through its side wall to form multiple openings, or ports, providing direct access to the exterior for fluid flowing through a common central lumen. The ports are disposed at several axial positions along the infusion section to provide distribution of the therapeutic fluid along a desired length of the bodily passage. However, fluids flowing through a tube flow more readily from ports offering the least flow resistance. The longer the flow path followed by the fluid in the central lumen, the higher the resistance and the higher the pressure drop ($\Delta P$) in the fluid. If the infusion section of this catheter has multiple ports or passageways the fluid flowing from each port exhibits resistance and a $\Delta P$ proportional to the fluid flow distance along the length of the central lumen. Thus, the fluid flowing to the more distal ports experiences higher $\Delta P$ than that flowing to the more proximal ports, and the fluid distribution is not uniform.

With respect to delivering various agents to specific regions of the body, the wall of a normal blood vessel includes an endothelial surface layer with an underlying connective tissue layer. When the wall of a blood vessel is diseased or injured, the endothelial surface layer breaks or tears. The break or lesion in the endothelial surface layer exposes collagenous connective tissue fibers to the blood flowing through the lumen of the blood vessel. Platelets present in the bloodstream adhere to the collagenous fibers, thereby initiating the coagulation cascade that results in a clot. The clot projects radially from the vessel wall into the lumen of the blood vessel and may cause turbulent flow.

Intravenous thrombolytic therapy breaks apart clots and restores laminar flow through the blood vessel and into other areas of the vascular system. Typically, intra-arterial thrombolytic therapy is provided by placing an infusion catheter or wire guide within the clotted lesion of a blood vessel so that a thrombolytic agent is infused into the vessel lumen in the region of the clot.

Conventional techniques utilize catheters and wire guides with multiple sideports intended for increasing the volume of the thrombolytic agent flowing into the bloodstream. For example, some infusion catheter sets include coaxially positioned inner and outer catheters, each with a number of sideports or infusion slits. Another coaxial infusion set includes an outer catheter with sideports and an inner wire guide with infusion holes. Yet other multiple sideport infusion sets include a catheter with sideports and a wire guide for extending through the lumen of the catheter and occluding the distal end hole of the catheter.

A problem with these multiple sideport devices is that most or all of the thrombolytic agent is diffused through only one or two proximal sideports, thereby limiting the surface area of the targeted blood vessel which could be treated by the released thrombolytic agent. As a result, the thrombolytic agent does not adequately mix with blood throughout the lesion. The relatively low concentration of the thrombolytic agent in the blood is insufficient to provide the desired therapeutic effect before being carried away in the bloodstream.

Furthermore, the uneven flow of the thrombolytic agent from the infusion sideports creates turbulence in the bloodstream. The turbulence can cause particles of the clot to fracture and flow farther along the arterial system into decreasing caliber blood vessels. Historically, treating tandem clots is more difficult and time consuming than the slow dissolution of one clot. Another difficulty encountered in treating a tandem clot is that the infusion device might not fit into the lumen of the blood vessel where the particle is wedged and occluding blood flow.

SUMMARY OF THE INVENTION

The present invention overcomes the aforementioned problems and relates to a medical device and more particularly a catheter that is capable of delivering a variety of fluids to designated areas of the human body at a controlled and uniform fluid discharge rate. The invention further relates to a catheter that is capable of delivering a variety of fluids to the human body. The invention further relates to a method for precisely predetermining the transverse cross-sectional area of fluid passageways which extend radially through the side wall of a tubular body as well as other parameters. In accordance with the present invention, a single lumen medical device for the uniform delivery rate of a fluid is provided wherein the device comprises:

a) an elongated tubular body having proximal and distal ends;

b) a plurality of longitudinally spaced fluid passageways which extend radially through the sidewall of the elongated tubular body and along the length of the sidewall wherein at least one of the spacing of the passageways along the length of the tubular body the fluid flow rate out of the tubular body or the pressure of the fluid in the tubular body at each passageway is predetermined; and the transverse cross-sectional area of the passageways are precisely predetermined to provide a controlled and uniform rate of discharge of fluid from the passageways, and c) means at the proximal end of the tubular body to direct the fluid into the lumen of the device.

Further in accordance with the present invention a single lumen tubular body providing uniform fluid flow therefrom; comprising:

a) an elongated tubular body having proximal and distal ends;

b) means at the proximal end of the tubular body to direct the fluid into the lumen; and c) a plurality of longitudinally spaced fluid passageways which extend radially through the sidewall of the elongated tubular body and along the length of the sidewall wherein the transverse cross sectional area of the passageways are predetermined to provide a controlled uniform rate of discharge of fluid from the tubular body wherein the spacing of the passageways is set at a constant value and the transverse cross sectional area of the passageways are predetermined by the method comprising;

i) means for determining the constant rate of flow $Q_i$ out of each $i^{th}$ passageway from the flow rate of the fluid into the lumen of the tubular body;

ii) means for determining the pressure $P_i$ at the $i^{th}$ passageway from the known pressure $P_{amb}$ outside the tubular body;

iii) means for calculating the diameter $D_i$ of each $i^{th}$ passageway from the known viscosity $\mu$ of the fluid directed into the proximal end of the tubular body according to the following formula:

$$D_i = \left( \frac{3840 \, \mu \, Q_i}{\pi (P_i - P_{amb})} \right)^{1/3}$$

is provided.

Still further in accordance with the present invention a method is provided for treating the human body through the vascular system of the body comprising:

a) advancing a guide wire through the region of the vascular system to the area requiring treatment;

b) advancing a single lumen catheter over the guide wire until the catheter extends into the region requiring treatment, the catheter comprising:

i) an elongated tubular body having proximal and distal ends;

ii) a plurality of longitudinally spaced fluid passageways which extend radially through the sidewall of the elongated tubular body and along the length of the sidewall wherein at least one of the spacing of the passageways, the fluid flow rate from the tubular body or the pressure of the fluid in the tubular body at each of the passageways is predetermined, and the transverse cross sectional area of the passageways are precisely predetermined to provide a controlled and uniform rate of discharge of fluid from the passageways, and iii) means at the proximal end of the tubular body to direct the fluid into the lumen, and c) directing treating fluid through the lumen of the catheter to discharge the treating fluid through the radially extending passageways at a uniform discharge rate.

Still further in accordance with the present invention a method is provided for producing a single lumen tubular body having a uniform rate of fluid discharge from passageways in the walls of the tubular body comprising:

a) forming a single lumen tubular body having proximal and distal ends from a flexible material; and b) forming passageways in the wall of the tubular body along its length wherein the transverse cross-sectional area of the passageways are predetermined according to the following formula:

$$D_i = \left( \frac{3840 \, \mu \, Q_i}{\pi (P_i - P_{amb})} \right)^{1/3}$$

wherein $D_i$ is the diameter of each $i^{th}$ passageway, $Q_i$ is the constant rate of flow of fluid discharged out of each $i^{th}$ passageway, $\mu$ is the viscosity of the fluid directed into the proximal end of the tubular body, $P_{amb}$ is the pressure outside the tubular body and $P_i$ is the pressure at each $i^{th}$ passageway and wherein the spacing of the $i^{th}$ passageway is set at a constant value.

Still further in accordance with the present invention, a medical device for delivering fluids into the body of a patient is described having fluid passageways formed in a section of the catheter where the transverse cross sectional area of the passageways increases from the proximal end section to the distal end section of the device. Also the boundaries of the section of the catheter containing the fluid passageways is indicated by radiopaque markers.

The foregoing and other features of the invention are hereinafter more fully described and particularly pointed out in the claims. The following description sets forth in detail certain illustrative embodiments of the invention, those being indicative, however, of but a few of the various ways in which the principles of the invention may be employed.

BRIEF DESCRIPTION OF THE DRAWINGS

The invention will be further described in connection with the attached drawing figures showing preferred embodiments of the invention including specific parts and arrangements of parts. It is intended that the drawings included as a part of this specification be illustrative of the preferred embodiment of the invention and should in no way be considered as a limitation on the scope of the invention.

FIG. 1 is a perspective view of a medical device according to one embodiment of the present invention.

FIG. 2 is a sectional view of the distal end of a medical device according to one embodiment of the present invention.

DETAILED DESCRIPTION

An exemplary embodiment of the elongated tubular body according to the present invention is a single lumen infusion catheter. A method has been developed to predetermine a controlled and uniform rate of discharge from the catheter or from segments or sections of the catheter. This exemplary catheter is illustrated in FIG. 1 where infusion catheter 10 includes elongated tubular body 12 having a proximal end 16 and distal end 14. A fluid, e.g., a therapeutic or diagnostic agent, may be introduced into the single lumen 20 to be discharged into the body through fluid passageways 18 at a controlled and uniform rate. The catheter further comprises an elongated section 19 having no fluid passageways and further comprises a distal radiopaque tip 11 and a proximal radiopaque band 15 or marker to indicate the boundary of the section of the catheter containing the fluid passageways 18. The radiopaque tip 11 may be molded into the catheter body from a molding composition comprising about 80% tungsten by weight. However, any known method for producing a radiopaque tip may be employed. Likewise, the radiopaque band 15 is preferably a metal band and is most preferably a platinum/iridium (Pt/Ir)metal alloy band. As with the radiopaque tip 11, any known metal or means to render the proximal boundary radiopaque may be employed.

Depending upon the particular application and fluid agent being infused, the rate of fluid discharge may vary at designated sections along the length of the catheter but at a controlled and uniform rate within each designated section. Moreover a guidewire, not shown, may be contained within the lumen 20 for the insertion and advancement of the catheter 10.

For infusion catheters, it is highly desirable to deliver the particular fluid, whether a therapeutic agent or a diagnostic agent, to the particular area of the body for treatment or diagnosis and that the fluid be delivered at a controlled and uniform rate of discharge. Not only is it important to control the rate of discharge of fluid to achieve the desired therapeutic effect or diagnostic result, but also to avoid or minimize damage to the body tissue by frictional or shear forces or by too high pressure or volume of fluid. To achieve the desired control and uniform rate of discharge of fluid from the passageways of the catheter, a method has been devised for predetermining the transverse cross-sectional area of the passageways, as well as the spacing of the passageways, the flow rate of the fluid discharged out of the passageways, and the fluid pressure at each of the passageways. By way of illustration, a three-hole or three-passageway catheter is shown in FIG. 2. The portion of tubular body 12 containing passageways 18 and lumen 20 in which guidewire 22 is contained and creating space 21 into which a fluid is delivered. In order to predetermine the rate of fluid discharge 24, and further identified herein as $Q_i$ from passageways 18 and their respective diameters or transverse cross-sectional areas 23A, 23B, 23C, the ambient pressure 26, given the designation and symbol $P_{amb}$ exterior to the catheter must be determined and the pressure $P_i$, 27A, 27B and 27C must also be determined. The spacing 25 of the passageways 18 is set at a constant value.

To further illustrate one embodiment according to the present invention the following exemplary determination is provided for a three-hole (passageway) catheter. Please recognize that this example is provided solely for the purposes of illustration of the present invention and is not intended to limit the scope of the invention in any manner.

The fluid in the catheter was assumed to have the properties of water at a temperature of 68° F. (20° C.). However, it is understood that the viscosity may vary with temperature and the appropriate values utilized to ensure uniform flow rates and laminar flow. The pressure and flow rate terms shown in FIG. 2 are:

$P_{amb}$ = ambient pressure outside the catheter $P_1, P_2, P_3$ = pressure in the tube at the three holes $Q_t$ = total flow rate through the catheter
= 50 to 150 ml/hr $Q_0$ = flow rate out of the end of the catheter $Q_1, Q_2, Q_3$ = flow rates out of the three holes The procedure used has three parts. The first step is to set the flow rates out of the side-holes 18 and the end-hole (not shown) as percentages of the total flow. The second step is to find the pressure in the tube at each hole. The last step is to find the size of the hole needed for the given flow. The second and third steps are repeated for each hole, starting with the hole closest to the end of the tube.

Since the flow rates out of the holes are desired to be equal and the flow rate out of the end should be small compared to the other flows, it is assumed, for the purposes of this illustration, that 30% of the total flow goes out of each hole and 10% out of the end.

To find the pressure at the inlet of the holes, some geometric data is needed. The first is the cross-sectional area of the annulus. It is:

$$A_c = \frac{\pi}{4}(D_0^2 - D_i^2) \qquad (1)$$

where:

$A_c$ = cross-sectional area of the annulus or fluid space 21
The wetted perimeter of annulus 21 is:

$$P_w = \pi(D_o + D_i) \qquad (2)$$

where:

$P_w$ = wetted perimeter of the annulus 21
The following parameters chosen for the purposes of this illustration.

$D_i$ = diameter of the guide wire 22 = inner diameter
of the annulus 21
= 0.035"

$D_0$ = inner diameter of the lumen 20 = outer diameter of
the annulus 21 and is for this example
= 0.048"

$t$ = thickness of the tube
= 0.0095"

$L_1$ = distance from the center of the first hole to the end
of the tube
= 1.57"

$L_1$ = distance from the center of the second hole to the
center of the first hole
= 1.57"

$L_1$ = distance from the center of the third hole to the
center of the second hole
= 1.57"

$D_1, D_2, D_3$ = diameters of the three holes 18 Equations (1) and (2) are valid even if the guidewire 22 is touching the tube wall since the area of contact is small. Even though the cross-section is not circular, it can be approximated as a circular cross-section with an effective diameter. This allows the use of equations derived for circular cross-sections. The effective diameter is called the hydraulic diameter and is defined as:

$$D_h = \frac{4 A_c}{P_w} \qquad (3)$$

where:

$D_h$ = hydraulic diameter
For an annular region, the hydraulic diameter reduces to the difference between the inner and the outer diameter.

Since the fluid velocity in the annulus is small and the changes in elevation are small, the equation for the pressure at the first hole is:

$$P_1 = P_{amb} + \frac{f \rho V_{a1}^2 L_1}{2 D_h} \qquad (4)$$

where:
f = friction factor
ρ = density of the fluid $V_{al}$=average velocity of the fluid in the annulus through the distance $L_1$, The velocity in the annulus is:

$$V_{al} = \frac{Q_{al}}{A_c} \tag{5}$$

where:

$Q_{al}$ = flow rate in the annulus through the distance $L_1$ $= Q_0$

The $Q_{a1}$ notation is used so that the same equations will be valid for other sections of the annulus.

The friction factor is a coefficient based on the flow conditions and the material of the tubing. Since the flow is laminar (as will be shown later), the friction factor is only a function of the flow conditions and is:

$$f = \frac{64}{Re_{al}} \tag{6}$$

where:

$Re_{al}$=Reynolds number in the annulus 21 through the distance $L_1$

The Reynolds number is a dimensionless number that describes the flow. It is defined as:

$$Re_{al} = \frac{\rho V_{al} D_h}{\mu} \tag{7}$$

where:

$\mu$=viscosity of the fluid

Substituting equations (3) and (5) into equation (7) gives:

$$Re_{al} = \frac{4\rho Q_{al}}{\mu P_w} \tag{8}$$

Substituting equation (8) into equation (6) gives:

$$f = \frac{16\mu P_w}{\rho Q_{al}} \tag{9}$$

Substituting equations (3), (5), and (9) into equation (4) gives:

$$\Delta P_1 = \frac{32\mu Q_{al} L_1}{D_h^2 A_c} \tag{10}$$

where:

$\Delta P_1$=change in pressure from the distal end of tube to hole 1

Using equation (10) the pressure difference between each hole can be found. In general, equation (10) is:

$$\Delta P_1 = \frac{32\mu Q_{al} L_1}{D_h^2 A_c} \tag{11}$$

where:

$\Delta P_1$ = change in pressure from hole $I-1$ to hole $I$ $Q_{ai}$ = flow rate in the annulus through the distance $L_1$ $= Q_0 + Q_1 + \ldots + Q_{i-1}$ The pressure at each hole is then:

$$P_i = P_{amb} + \Delta P_1 + \ldots + \Delta P_i \tag{12}$$

With the pressure known at each hole, the diameters can be calculated.

Several assumptions were made about the flow through the holes. The first is that the flow through the holes causes no pressure drop in the fluid in the annulus. The second is that the flow through the holes can be treated like flow through an elbow. The losses through an elbow can be approximated by the frictional losses through a length of tubing 30 diameters long. The change in pressure from one side of the hole to the other is:

$$P_1 - P_{amb} + \frac{f_i \rho V_i^2 \cdot (30 D_i)}{2 D_i} \tag{13}$$

where:

$V_i$=velocity through hole I

The velocity through the hole is:

$$V_i = \frac{Q_i}{A_i} = \frac{4Q_i}{\pi D_i^2} \tag{14}$$

where:

$A_i$=cross-sectional area of hole I

Substituting equation (14) into equation (7) gives:

$$Re_i = \frac{4\rho Q_i}{\pi \mu D_i} \tag{15}$$

where:

$Re_i$=Reynolds number through hole I

Substituting equations (6), (14) and (15) into equation (13) gives:

$$P_i - P_{amb} = \frac{3840\mu Q_i}{\pi D_i^3} \tag{16}$$

Solving equation (16) for $D_i$ gives:

$$D_i = \left(\frac{3840\mu Q_i}{\pi(P_i - P_{amb})}\right)^{1/3} \tag{17}$$

Using equation (17), the diameters of the holes 18 may be found.

EXAMPLE: THREE HOLE CATHETER

To demonstrate the procedure derived in the Analysis section, the case shown in FIG. 2 will be analyzed. The total flow rate is 100 ml/hour or $9.809 \times 10^{-7}$ ft$^3$/s. Ten percent of the flow goes out of the end and 30% goes out of each hole. From equation (1), the cross-sectional area of the annulus is:

$$A_c = \frac{\pi}{4}((0.048)^2 - (0.035)^2) = 8.474 \times 10^{-4} \text{ in.} \quad (18)$$

From equation (2), the wetted perimeter is:

$$P_w = \pi(0.048+0.035) = 0.261 \text{ in.} \quad (19)$$

From equation (3), the hydraulic diameter is:

$$D_h = \frac{4(8.474 \times 10^{-4})}{0.261} = 0.013 \text{ in.} \quad (20)$$

With the basic geometric information calculated, the pressures and diameters can be calculated. The fluid properties are needed first. For water at 68° F., the density is 62.5 lbm/ft³ and the viscosity is $67.6 \times 10^{-5}$ lbm/ft s. From equation (11), the pressure at hole 1 is:

$$P_1 - P_{amb} = \frac{32(12)^3(67.6 \times 10 - 5)(9.809 \times 10^{-8})(1.57)}{(32.2)(0.013)^2(8.474 \times 10^{-4})} = 1.248 \frac{\text{lbf}}{\text{ft}^2} \quad (21)$$

The 32.2 term in the denominator of equation (21) is the unit conversion factor $g_c$. The value of $g_c$ is 32.2 ft lbm/lbf s². This term is present in most of the example equations. The diameter of hole 1, from equation (17), is:

$$D_1 = 12\left(\frac{3840(67.6 \times 10^{-5})(2.943 \times 10^{-7})}{\pi(1.248)(32.2)}\right)^{1/3} = 0.0219 \text{ in.} \quad (22)$$

We need to check to see if the flow is laminar in all of the regions to verify that the correct equations were used. Flow is laminar if the Reynolds number is less than 2300. From equation (8), the Reynolds number in the annulus through $L_1$ is:

$$Re_{a1} = \frac{4(62.5)(9.809 \times 10^{-8})(12)}{(67.6 \times 10^{-5})(0.261)} = 1.67 \quad (23)$$

From equation (15), the Reynolds number through hole 1 is:

$$Re_1 = \frac{4(62.5)(2.943 \times 10^{-7})(12)}{\pi(67.6 \times 10^{-5})(0.0219)} = 18.98$$

The flow is very laminar out of hole 1 and through the annulus from hole 1 to the end of the tube.

Table 1 summarizes the calculations for the remaining two holes. It is noted that the Reynolds number is less than 2300 in all regions indicating laminar flow through these regions.

TABLE 1

Summary of calculations for three hole catheter.

| Hole I | 1 | 2 | 3 |
|---|---|---|---|
| $Q_i$ (ft³/s) | $2.943 \times 10^{-7}$ | $2.943 \times 10^{-7}$ | $2.943 \times 10^{-7}$ |
| $Q_{ai}$ (ft³/s) | $9.809 \times 10^{-8}$ | $3.924 \times 10^{-7}$ | $6.866 \times 10^{-7}$ |
| $L_i$ (in.) | 1.57 | 1.58 | 1.57 |
| $\Delta P_i$ (lbf/ft²) | 1.248 | 5.025 | 8.738 |
| $P_i - P_{amb}$ (lbf/ft²) | 1.248 | 6.273 | 15.011 |
| $D_i$ (in.) | 0.0219 | 0.0128 | 0.0095 |
| $Re_{ai}$ | 1.67 | 6.67 | 11.67 |
| $Re_i$ | 18.98 | 32.51 | 43.49 |

While the foregoing examples illustrate specific embodiments according to the present invention, numerous variations of the catheters described above are considered to be within the scope of the invention. For example, the passageways for discharging the fluid may be arranged in a number of ways including linearly along the one side of the catheter, there may be for example, two opposing passageways 180° with respect to each passageway on either side of the catheter, there may be four passageways disposed within the same plane and arranged 90° with respect to each passageway and the like or in one preferred embodiment the passageways may be spiraled 90° along the length of the catheter. The passageways may be formed by several different techniques depending upon the materials out of which the catheter is formed as well as the particular application or use of the particular catheter. In one preferred embodiment, the fluid passageways are drilled with a laser, particularly in catheters where very small diameters or transverse cross-sectional areas are required. While the passageways are generally cylindrical in shape; they may have any geometric shape, e.g., conical, cubic and the like. Also, the catheter may be formed by known molding techniques, e.g., extrusion, or injection molding. Another consideration is that the catheter may have a varying wall thickness along its length.

The catheter may be formed from conventional flexible materials. For example, such materials that may find application for preparing the catheters according to the present invention are polyethylene, polypropylene, polyethylene terephthalte, nylon, and various silicon based polymers. As a most preferred embodiment according to present invention, the catheter is prepared from nylon. Also, the exterior wall of the catheter may contain a hydrophlic coating, e.g., polyvinyl pyrrolidone, polyethylene glycol, polyethylene oxide, and the like, to improve the ease of inserting the catheter in the body of the patient.

The catheter according to present invention may be utilized, for example, to infuse such agents as chemotherapeutic agents, thrombolytics agents, antibiotics, or diagnostic agents, e.g., dyes and radioactive materials, or more inert fluids such as heparin, saline solution and the like. Moreover, the technique of predetermining the diameter and spacing of the fluid passageways may be employed in producing other elongated tubular bodies for use in industry and introducing fluids into a system, e.g. inert gases into a chemical reaction, fluid reactants into a chemical reaction system and the like.

Although the invention has been shown and described with respect to preferred embodiments, equivalent alterations and modifications of the components and methods of the invention may occur to those skilled in the art upon reading and understanding this specification. The present invention includes all such equivalent alterations and modifications, and it is limited only by the scope of the claims that follow.

What is claimed is:

1. A single lumen medical device for the uniform delivery rate of a fluid; comprising:

a) an elongated tubular body having proximal and distal ends and having a single lumen formed therein;

b) a plurality of longitudinally spaced fluid passageways which extend radially through the sidewall of the elongated tubular body and along the length of the sidewall wherein the spacing of the passageways along the length of the tubular body and the transverse cross-sectional areas of the passageways are selected so as to provide a laminar fluid flow discharge and a uniform rate of discharge of fluid from the passageways at a total rate of discharge of fluid as great as at least about 150 ml/hr through the elongated tubular body, and c) means at the proximal end of the tubular body to direct the fluid into the lumen.

2. The device according to claim 1 wherein said fluid is a therapeutic agent.

3. The device according to claim 1 wherein said fluid is a diagnostic agent.

4. The device according to claim 1 wherein said elongated tubular body contains a guide wire within the lumen.

5. The device according to claim 1 wherein the transverse cross-sectional shape of the fluid passageways is cylindrical.

6. The device according to claim 1 wherein the transverse cross-sectional shape of the fluid passageways is conical.

7. The device according to claim 1 wherein the fluid passageways are spiraled 90° along the length of the tubular body.

8. The device according to claim 1 wherein at least two passageways are located in a single cross-sectional plane of the tubular body.

9. The device according to claim 1 wherein the tubular body is segmented with respect to different fluid discharge rates wherein the discharge from the passageways within each segment is controlled and uniform.

10. The device according to claim 1 wherein said tubular body comprises a flexible material and wherein the distal tip of the tubular body is radiopaque and a radiopaque band is positioned at a proximal terminus of the fluid passageways in order to mark the boundaries of a section of the tubular body containing said fluid passageways.

11. The device according to claim 10 wherein said flexible material is nylon and said proximal radiopaque band is comprised of Pt and Ir.

12. The device according to claim 1 wherein said transverse cross-sectional, area of the passageways are predetermined according to the following formula:

$$D_i = \left(\frac{3840 \mu Q_i}{\pi(P_i - P_{amb})}\right)^{1/3}$$

wherein $D_i$ is the diameter of each $i^{th}$ passageway, $Q_i$ is the constant rate of flow of fluid discharged out of each passageway, $\mu$ is the viscosity of the fluid directed into the proximal end of the tubular body, $P_{amb}$ is the pressure outside the tubular body and $P_i$ is the pressure at each $i^{th}$ passageway and wherein the spacing of the $i^{th}$ passageways is set at a constant value.

13. The device according to claim 1 wherein the transverse cross-sectional areas are increasingly larger for the passageways located at the distal end of the tubular body as compared to the passageways located at the proximal end of the tubular body.

14. The device according to claim 1 wherein the flow of the fluid within the lumen of the tubular body is laminar.

15. The device according to claim 1 wherein the wall thickness of the tubular body varies along the length of the tubular body and the exterior wall of the catheter comprises a hydrophilic coating.

16. A device according to claim 1 wherein said device is a catheter produced from nylon containing a guide wire within the lumen of the catheter, and said fluid passageways are cylindrical shaped and spiraled at 90° with respect to each other along the length of a section of said catheter and wherein the boundary of the section of the catheter containing the fluid passageways is marked by a radiopaque tip at the distal end and a Pt/Ir band at the proximal terminus of the fluid passageways and the transverse cross-sectional area of the fluid passageways are predetermined according to the following formula:

$$D_i = \left(\frac{3840 \mu Q_i}{\pi(P_i - P_{amb})}\right)^{1/3}$$

wherein $D_i$ is the diameter of each $i^{th}$ passageway, $Q_i$ is the constant rate of flow of fluid discharged out of each passageway, $\mu$ is the viscosity of the fluid directed into the proximal end of the tubular body, $P_{amb}$ is the pressure outside the tubular body and $P_i$ is the pressure at each $i^{th}$ passageway and wherein the spacing of the $i^{th}$ passageways is set at a constant value.

17. A method for treating the human body through the vascular system of the body comprising:

a) advancing a guide wire through the region of the vascular system to the area requiring treatment; and b) advancing a single lumen catheter over the guide wire until the catheter extends into the region requiring treatment, the catheter comprising:

i) an elongated tubular body having proximal and distal ends and having a single lumen formed therein, ii) a plurality of longitudinally spaced fluid passageways which extend radially through the sidewall of the elongated tubular body and along the length of the sidewall wherein the spacing of the passageways and the transverse cross sectional areas of the passageways are selected so as to provide a laminar fluid flow discharge and a uniform rate of discharge of fluid from the passageways at a total rate of discharge of fluid as great as at least about 150 ml/hr through the elongated tubular body, and iii) means at the proximal end of the tubular body to direct the fluid into the lumen; and c) directing treating fluid through the lumen of the catheter to discharge the treating fluid through the radially extending passageways; whereby the discharge of the treating fluid is at a uniform discharge rate.

18. The method according to claim 17 wherein said fluid is a therapeutic agent.

19. The method according to claim 17 wherein said fluid is a diagnostic agent.

20. The method according to claim 17 wherein the transverse cross-sectional shape of the fluid passageways is cylindrical or conical.

21. The method according to claim 17 wherein passageways are spiraled 90° along the length of the tubular body.

22. The method according to claim 17 wherein the tubular body is segmented with respect to different fluid discharge rates wherein the discharge from the passageways within each segment is controlled and uniform.

23. The method according to claim 17 wherein the transverse cross-sectional areas are increasingly larger for the passageways located at the distal end of the tubular body as compared to the passageways located at the proximal end of the tubular body.

24. The method according to claim 17 wherein the flow of the fluid within the lumen of the tubular body is laminar.

25. A method for treating the human body through the vascular system of the body comprising:

a) advancing a guide wire through the region of the vascular system to the area requiring treatment; and b) advancing a single lumen catheter over the guide wire until the catheter extends into the region requiring treatment, the catheter comprising:

i) an elongated tubular body having proximal and distal ends and having a single lumen formed therein, ii) a plurality of longitudinally spaced fluid passageways which extend radially through the sidewall of the elongated tubular body and along the length of the sidewall wherein the spacing of the passageways and the transverse cross sectional areas of the passageways are selected so as to provide a laminar fluid flow discharge and a uniform rate of discharge of fluid from the passageways at a total rate of discharge of fluid as great as at least about 150 ml/hr through the elongated tubular body, and iii) means at the proximal end of the tubular body to direct the fluid into the lumen; and c) directing treating fluid through the lumen of the catheter to discharge the treating fluid through the radially extending passageways, whereby the discharge of the treating fluid is at a uniform discharge rate;

wherein said transverse cross-sectional areas of the passageways are predetermined according to the following formula:

$$D_i = \left( \frac{3840 \mu Q_i}{\pi (P_i - P_{amb})} \right)^{1/3}$$

wherein $D_i$ is the diameter of each $i^{th}$ passageway, $Q_i$ is the constant rate of flow of fluid discharged out of each passageway, $\mu$ is the viscosity of the fluid directed into the proximal end of the tubular body, $P_{amb}$ is the pressure outside the tubular body and $P_i$ is the pressure at each $i^{th}$ passageway and wherein the spacing of the $i^{th}$ passageways is set at a constant value.

26. A method for producing a single lumen tubular body having a uniform rate of fluid discharge from passageways in the walls of the tubular body comprising:

a) forming a single lumen tubular body having proximal and distal ends from a flexible material; and b) forming passageways in the wall of the tubular body along its length wherein the transverse cross-sectional area of the passageways are predetermined according to the following formula:

$$D_i = \left( \frac{3840 \mu Q_i}{\pi (P_i - P_{amb})} \right)^{1/3}$$

wherein $D_i$ is the diameter of each $i^{th}$ passageway, $Q_i$ is the constant rate of flow of fluid discharged out of each passageway, $\mu$ is the viscosity of the fluid directed into the proximal end of the tubular body, $P_{amb}$ is the pressure outside the tubular body and $P_i$ is the pressure at each $i^{th}$ passageway and wherein the spacing of the $i^{th}$ passageway is set at a constant value.

27. The method according to claim 26 wherein said flexible material is nylon.

28. The method according to claim 26 wherein said tubular body is a catheter.

29. The method according to claim 26 wherein said tubular body is formed by extrusion and said passageways are drilled with a laser according to said formula.

30. The method according to claim 26 wherein the transverse cross-sectional areas are larger for the passageways near the distal end of tubular body as compared to the passageways near to the proximal end.

* * * * *